United States Patent [19]

Sorrentino

[11] Patent Number: 5,100,898

[45] Date of Patent: * Mar. 31, 1992

[54] ANTITUSSIVE LIQUID COMPOSITIONS CONTAINING DYCLONINE

[75] Inventor: James V. Sorrentino, Wilton, Conn.

[73] Assignee: Richardson-Vicks Inc., Shelton, Conn.

[*] Notice: The portion of the term of this patent subsequent to Jun. 5, 2007 has been disclaimed.

[21] Appl. No.: 590,319

[22] Filed: Sep. 28, 1990

Related U.S. Application Data

[63] Continuation of Ser. No. 470,194, Jan. 25, 1990, abandoned.

[51] Int. Cl.$^5$ .................. A61K 31/44; A61K 31/445; A61K 31/135; A61K 31/13
[52] U.S. Cl. ................. 514/281; 514/289; 514/291; 514/317; 514/648; 514/659; 514/817; 514/850
[58] Field of Search .............. 514/289, 317, 291, 281, 514/648, 659, 850, 817

[56] References Cited

U.S. PATENT DOCUMENTS

| | | | |
|---|---|---|---|
| 2,771,391 | 11/1956 | Bockstahler | 514/317 |
| 2,868,689 | 1/1959 | Florestano | 514/317 |
| 4,316,888 | 2/1982 | Nelson | 424/602 |
| 4,446,140 | 5/1984 | Nelson | 424/260 |
| 4,639,367 | 1/1987 | Mackles | 424/45 |
| 4,752,465 | 6/1988 | Mackles | 424/45 |
| 4,808,410 | 2/1989 | Sorrentino | 424/435 |
| 4,889,709 | 12/1989 | Mackles | 424/45 |
| 4,892,877 | 1/1990 | Sorrentino | 514/289 |
| 4,931,473 | 6/1990 | Kelleher et al. | 514/688 |
| 4,971,798 | 11/1990 | Coia et al. | 424/440 |

*Primary Examiner*—Glennon H. Hollrah
*Assistant Examiner*—Gary E. Hollinden
*Attorney, Agent, or Firm*—David K. Dabbiere; Anthony D. Sabatelli; Douglas C. Mohl

[57] ABSTRACT

Novel antitussive and anesthetic liquid compositions of matter for oral use comprising an effective oral antitussive drug and dyclonine; and method of using same.

12 Claims, No Drawings

ANTITUSSIVE LIQUID COMPOSITIONS CONTAINING DYCLONINE

This is a continuation of application Ser. No. 470,194, filed on Jan. 25, 1990, now abandoned.

TECHNICAL FIELD

This invention is directed to improved antitussive swallowable liquid compositions for oral use.

BACKGROUND OF THE INVENTION

Oral cough preparations, such as syrups, solutions, suspensions and the like, containing an effective antitussive agent have long been used for the symptomatic relief of coughs. The most popular of such preparations contain either dextromethorphan or its hydrobromide salt or codeine or its sulfate salt as the active antitussive agent.

Oral sore throat preparations, such as lozenges, sprays, solutions and the like, containing topical anesthetic/analgesic agents have long been used for the symptomatic relief of sore throat. Dyclonine HCl, a member of a class of compounds known as β-aminopropiophenones and which is chemically denoted as 3-piperidino-4'-butoxypropiophenone hydrochloride, is a well known anesthetic/analgesic agent for topical use on the mucous membranes of the mouth and throat (see Federal Register, Vol. 47, No. 101, Proposed Rules, pages 22810-22813, 1982). Previous dosage forms of administration have included aqueous solutions of 0.1% dyclonine for use as a mouthwash, rinse or gargle, which is expelled from the oral cavity after use, and as a throat spray. Such forms provide topical application of an effective dose of dyclonine directly to the mucous membranes or mouth tissues. The ensuing anesthesia/analgesia lasts so long as an effective concentration of the dyclonine is supplied to the site of action. As the dyclonine is washed away, e.g., by saliva, the anesthetic/analgesia action recedes. Other dosage forms containing dyclonine HCl include solid lozenges containing 1.2 mg per lozenge for children and 3.0 mg per lozenge for adults (see Physicians' Desk Reference for Non-prescription Drugs, 8th Ed., 1987, pages 518-9). The benefit of dyclonine HCl is that it provides long-acting topical anesthetic relief. The mode of action is believed to be that it desensitizes sensory nerve receptors present in the mucous membranes of the throat and oral cavity to exert its local anesthetic effect.

The use of certain acids, particularly citric acid, to stabilize dyclonine HCl in anesthetic lozenges is reported in U.S. Pat. No. 4,139,627 to Lane et al., issued Feb. 13, 1979. The use of saccharin to stabilize dyclonine is disclosed in U.S. Ser. No. 311,155, filed Feb. 15, 1989 to Kelleher et al. In addition to its anesthetic-/analgesic properties, dyclonine HCl is reported to possess antimicrobial activity. In this regard, U.S. Pat. No. 2,868,689 to Florestane et al., issued Jan. 13, 1959 discloses stabilized aqueous preparations of dyclonine HCl (0.1-5%) having topical anesthetic and antimicrobial action, the stabilization aspect being provided by the addition of chlorobutanol (0.1-0.5%).

Solid lozenge forms of the antitussive agent, dextromethorphan hydrobromide (10 mg), and phenol (32.5 mg) are known to be commercially available in Canada for the respective systemic treatment of coughs and local treatment of accompanying irritated throat. Also in British Patent No. 1,144,915, medicinal two-phase solid pastille forms containing (among others) dextromethorphan and phenol in the separate phases are disclosed for the respective treatment of cough and sore throat relief. Such solid lozenge and pastille forms require the action of saliva over an extended period of time for dissolution of the solid form, thereby effectuating release of the respective active ingredients and prolonged contact of phenol at the mucosal membrane throat site.

To date, however, applicants herein are unaware of any combination of an effective oral antitussive drug and dyclonine in a liquid composition for administration by immediate swallowing.

It has now been found that the combined use of dyclonine and an oral antitussive drug in a swallowable liquid provides improved relief to an individual afflicted with cough or cough and associated sore throat, without the aforementioned need for prolonged contact with mucosal membranes of the throat and oral cavity.

SUMMARY OF THE INVENTION

The present invention relates to liquid pharmaceutical compositions of matter for the treatment of cough or cough and associated sore throat comprising, per 5-30 ml dose an aqueous-based orally acceptable pharmaceutical carrier, an effective antitussive swallowable amount of an oral antitussive drug, and from about 5 to about 100 milligrams (mg), preferably from about 5 to about 50 mg and most preferably from about 5 to about 12 mg, of dyclonine. Also provided are methods of using the same.

All percentages and ratios used herein are by weight and all measurements at 25° C. unless otherwise indicated.

DESCRIPTION OF THE INVENTION

More specifically, the subject invention provides a liquid pharmaceutical composition of matter for the treatment of cough or cough and associated sore throat in a human afflicted with same. Said composition comprises, per dose of 5-30 milliliters, an aqueous-based orally acceptable pharmaceutical carrier, an effective antitussive swallowable amount of an oral antitussive drug, and from about 5 to about 100 milligrams (mg), preferably from about 5 to about 50 mg and most preferably from about 5 to about 12 mg, of dyclonine, said composition having a pH of less than about 5, preferably less than about 4 and most preferably less than about 3.5.

The hydrochloride salt of dyclonine is preferred since it is readily available; however, other pharmaceutically acceptable salts of dyclonine, such as those formed with hydrobromic acid, fumaric acid, malic acid, tartaric acid, lactic acid, adipic acid, phosophoric acid, sulfuric acid, methane sulfonic acid, naphthalene disulphonic acid, acetic acid and the like may also be utilized in a similar manner.

As used herein, the term "oral antitussive drug" means a drug that is taken by mouth and acts systemically to relieve cough (see Federal Register, Vol. 52, No. 155, 12 August 1987, page 30055).

The choice of a particular oral antitussive drug is not critical. Well recognized oral antitussive drugs include, but are not limited to, for example, the non-narcotic type such as dextromethorphan and its acid addition salts, preferably the hydrobromide, chlophedianol hydrochloride, carbetapentane citrate, caramiphen edisylate, diphenhydramine and its hydrochloride salt, noscapine hydrochloride and the like, and the non-addictive narcotic type such as codeine and its sulfate or/phosphate salts, hydrocodone and its bitartrate salt, hydromorphone hydrochloride, and the like. The usual adult dosage for such antitussives, which may also be utilized per dose in the subject compositions, are indicated in Table I.

TABLE I

| Oral Antitussive Drug | Usual Adult Dose (mg) |
|---|---|
| Dextromethorphan HBr | 10-30 |
| Chlophedianol HCl | 15-25 |
| Carbetapentane citrate | 15-30 |
| Caramiphen edisylate | 15-20 |
| Noscapine HCl | 15-30 |
| Diphenhydramine HCl | 15-25 |
| Codeine sulfate | 10-20 |
| Hydrocodone bitartrate | 5-10 |
| Hydromorphone HCl | 2 |

The highly advantageous properties of the compositions of this invention are demonstrated by their improved anti-cough effectiveness, for example, by the method of E. W. Packman and S. J. London described in Current Therapeutic Research, Vol. 21, No. 6, June 1977, page 855. The methodology involves the quantitative measurement of the effect of an antitussive preparation on cough artificially induced in normal healthy subjects by a citric acid aerosol at various intervals.

The subject compositions surprisingly provide marked anti-cough effectiveness and also provide fast-acting and effective relief of accompanying irritated or sore throat even though the subject composition is swallowed in the normal fashion, as opposed to the heretofore usage of dyclonine locally over a period of time, for example, by means of a spray, gargle, lozenge and the like. It is surprisingly found that, by the simple act of completely swallowing the subject composition, which provides minimal contact time with the mucosal membranes of the throat and oral cavity, the therapeutic anesthetic effect of dyclonine is still exerted promptly.

The present invention thus provides a method of treating cough or cough and associated sore throat in a human afflicted with said symptoms comprising the oral administration to said human, by direct swallowing, of at least one 5-30 ml dose of a liquid pharmaceutical 1 composition having a pH of less than about 5 comprising, per 5-30 ml dose, water, an effective antitussive amount of oral antitussive drug, from about 5 to about 100 milligrams of dyclonine, and, preferably, from about 5 to about 75 volume percent of a co-solvent.

Since many of the oral antitussive drugs are generally used in the form of a water-soluble salt, they can be readily incorporated into conventional aqueous-based cough syrups and solution formulations. Water insoluble or difficultly soluble antitussives, generally in base form, may also be incorporated into aqueous-based orally acceptable pharmaceutical carriers such as dispersions, suspensions, oil-in-water emulsions and the like by means of suitable dispersing, suspending or emulsifying agents, respectively, which are readily apparent to those skilled in the art of pharmaceutical formulations.

In preparing the pharmaceutical compositions of the present invention, the oral antitussive drug and dyclonine components are incorporated into an aqueous-based orally acceptable pharmaceutical carrier consistent with conventional pharmaceutical practices. An "aqueous-based orally acceptable pharmaceutical carrier" is one wherein the entire or predominant solvent content is water. Typical carriers include simple aqueous solutions, syrups, dispersions and suspensions, and aqueous based emulsions such as the oil-in-water type. The most preferred carrier is the commonly used syrup form, an aqueous solution of high sugar content. While the amount of water in the compositions of this invention can vary over quite a wide range depending upon the total weight and volume of the two essential active ingredients and other optional non-active ingredients, the total water content, based on the weight of the final composition, will generally range from about 20 to about 75%, and, preferably, from about 20 to about 40%, by weight/volume.

Although water itself may make up the entire carrier, typical cough formulations preferably contain one or more of a co-solvent, for example, ethyl alcohol, propylene glycol, glycerin, polyethylene glycol and the like, to assist solubilization and incorporation of water insoluble ingredients, flavoring oils and the like into the composition. In general, therefore, the compositions of this invention preferably contain from about 5 to about 75 volume/volume percent and, most preferably, from about 5 to about 25 volume/volume percent, of a co-solvent.

To provide and maintain the subject compositions at a pH of less than about 5 and preferably less than about 3.5, buffers consistent with conventional pharmaceutical practices are generally utilized such as, for example, sodium citrate buffer and sodium phosphate buffer and the like.

The compositions of this invention may optionally contain one or more other known therapeutic agents, particularly those commonly utilized in cough/cold preparations, such as, for example, a decongestant such as pseudoephedrine hydrochloride, phenylephedrine hydrochloride and ephedrine hydrochloride; an analgesic such as acetaminophen and ibuprofen; an expectorant such as glyceryl guaiacolate, terpin hydrate and ammonium chloride; and an antihistamine such as chlorpheniramine maleate, doxylamine succinate, bromphenirame maleate and diphenhydramine hydrochloride.

Other optional ingredients well known to the pharmacist's art may also be included in amounts generally known for these ingredients, for example, natural or artificial sweeteners, flavoring agents, colorants and the like to provide a palatable and pleasant looking final product; antioxidants, for example, butylated hydroxy anisole or butylated hydroxy toluene, and preservatives, for example, methyl or propyl paraben or sodium or potassium benzoate to prolong and enhance shelf life.

The following non-limiting examples illustrate embodiments of the subject invention wherein both essential and optional ingredients are combined. It is to be understood that these examples are for illustrative purposes only and are not to be construed as limiting the scope of the invention thereto.

EXAMPLE 1

A stable liquid composition for oral administration is prepared by combining the following ingredients:

| Ingredients | Amount/10 ml Dose |
|---|---|
| Invert syrup, medium | 8.5 g |
| Sodium citrate, hydrous | 13.0 mg |
| Citric Acid | 60.0 mg |
| Potassium sorbate | 10.0 mg |

-continued

| Ingredients | Amount/10 ml Dose |
| --- | --- |
| Absolute alcohol | 1.00 ml |
| Propylene glycol | 1.16 g |
| Dyclonine HCl | 9.0 mg |
| Dextromethorphan HBr | 30.0 mg |
| Chlorpheniramine maleate | 4.0 mg |
| Colorant | 0.5 mg |
| Flavorants | 0.03 ml |
| Purified water, q.s. ad | 10.00 ml |

EXAMPLE 2

A stable liquid composition for oral administration is prepared by combining the following ingredients:

| Ingredients | Amount/15 ml Dose |
| --- | --- |
| Liquid sugar (66% sucrose in water) | 12.0 g |
| Potassium sorbate | 15.0 mg |
| Sodium citrate, hydrous | 30.0 mg |
| Citric acid, anhydrous | 90.0 mg |
| Sodium saccharin | 30.0 mg |
| Propylene glycol | 2.25 g |
| Dextromethorphan HBr | 30.00 mg |
| Psuedoephedrine HCl | 60.00 mg |
| Absolute alcohol | 1.50 ml |
| Dyclonine HCl | 9.0 mg |
| Guaifenesin | 200.00 mg |
| Menthol | 22.50 mg |
| Colorant | 0.75 mg |
| Flavorants | 0.05 ml |
| Purified water | 15.00 ml |

EXAMPLE 3

A stable liquid composition for oral administration is prepared by combining the following ingredients:

| Ingredients | Amount/15 ml Dose |
| --- | --- |
| Liquid sugar | 12.00 g |
| Potassium sorbate | 15.00 mg |
| Sodium citrate, hydrous | 20.00 mg |
| Citric acid, anhydrous | 90.00 mg |
| Sodium saccharin | 30.00 mg |
| Propylene glycol | 2.25 g |
| Dextromethorphan HBr | 30.00 mg |
| Absolute alcohol | 1.50 ml |
| Dyclonine HCl | 9.00 mg |
| Colorant | 0.75 mg |
| Flavorant | 0.05 ml |
| Purified water q.s. ad | 15.00 ml |

EXAMPLE 4

A stable liquid composition for oral administration is prepared by combining the following ingredients:

| Ingredients | Amount/5 ml Dose |
| --- | --- |
| Liquid sugar | 4.0 g |
| Potassium sorbate | 5.0 mg |
| Sodium citrate, hydrous | 6.5 mg |
| Citric acid, anhydrous | 30.0 mg |
| Sodium saccharin | 10.00 mg |
| Propylene glycol | 750.0 mg |
| Carbetapentane citrate | 30.0 mg |
| Absolute Alcohol | 0.50 ml |
| Dyclonine HCl | 9.00 mg |
| Flavorant | 0.02 ml |
| Colorant | 0.25 mg |
| Purified water, q.s. ad | 5.0 ml |

EXAMPLE 5

A stable liquid composition for oral administration is prepared by combining the following ingredients:

| Ingredients | Amount/5 ml Dose |
| --- | --- |
| Liquid sugar | 24.0 g |
| Potassium sorbate | 30.0 mg |
| Sodium citrate, hydrous | 6.5 mg |
| Citric acid, anhydrous | 30.0 mg |
| Sodium saccharin | 60.00 mg |
| Propylene glycol | 4.5 mg |
| Codeine sulfate | 15.0 mg |
| Absolute Alcohol | 3.00 ml |
| Dyclonine HCl | 9.00 mg |
| Flavorant | 0.10 ml |
| Colorant | 1.50 mg |
| Purified water, q.s. ad | 30.0 ml |

What is claimed

1. A liquid pharmaceutical composition of matter for use in the treatment of cough or cough and associated sore throat comprising, per 5–30 ml does:
   (a) an aqueous-based orally acceptable pharmaceutical carrier;
   (b) an effective antitussive amount of an oral antitussive drug selected from the group consisting of dextromethorphan, acid addition salts of dextromethorphan, chlophendianol hydrochloride, carbetapentane citrate, caramiphen edisylate, diphenydramine, diphenydramine hydrochloride, noscapine hydrochloride, codeine, codeine sulfate, codeine phosphate, hydrocodone, hydrocodone bitartrate, and hydromorphone hydrochloride;
   (c) from about 5 to about 100 milligrams of dyclonine or a pharmaceutically-acceptable salt thereof; and
   (d) from about 5 to about 75 volume/volume percent of co-solvent.

2. The composition of claim 1 wherein (b) is from about 10 to about 30 mg of dextromethorphan hydrobromide and (c) is from about 5 to about 12 mg of dyclonine or a pharmaceutically-acceptable salt thereof; and wherein said composition has a pH of less than about 5.

3. The composition of claim 1 wherein said co-solvent in (d) is a member selected from the group consisting of ethyl alcohol, glycerin, propylene glycol and polyethylene glycol and mixtures thereof.

4. A liquid pharmaceutical composition of matter for use in the treatment of coughs and associated sore throat, by direct swallowing, comprising, per 5–30 ml dose:
   (a) from about 20 to about 75% of water by weight/volume;
   (b) an effective amount of an oral antitussive drug selected from the group consisting of dextromethorphan, acid addition salts of dextromethorphan, chlophendianol hydrochloride, carbetapentane citrate, caramiphen edisylate, diphenydramine, diphenhydramine hydrochloride, noscapine hydrochloride, codeine, codeine sulfate, codeine phosphate, hydrocodone, hydrocodone bitartrate, and hydromorphone hydrochloride;
   (c) from about 5 to about 100 mg of dyclonine or a pharmaceutically-acceptable salt thereof; and
   (d) from about 5 to about 75 volume/volume percent of a co-solvent.

5. The composition of claim 4 wherein (b) is from about 10 to about 30 mg of dextromethorphan hydrobromide and (c) is from about 5 to about 12 mg of dyclonine or a pharmaceutically-acceptable salt thereof; and wherein said composition has a pH of less than about 5.

6. The composition of claim 5 wherein (a) is from about 20 to about 40% by weight of water.

7. A method of treating cough or cough and associated sore throat in a human afflicted with same which comprises orally administering to said human, by direct swallowing, of at least one 5-30 ml dose of a liquid pharmaceutical composition of matter comprising, per 5-30 ml dose;

(a) an aqueous-based orally acceptable pharmaceutical carrier;

(b) an effective antitussive amount of oral antitussive drug selected from the group consisting of dextromethorphan, acid addition salts of dextromethorphan, chlophendianol hydrochloride, carbetapentane citrate, caramiphen edisylate, diphenydramine, diphenhydramine hydrochloride, noscapine hydrochloride, codeine, codeine sulfate, codeine phosphate, hydrocodone, hydrocodone bitartrate, and hydromorphone hydrochloride;

(c) from about 5 to about 100 mg of dyclonine or a pharmaceutically-acceptable salt thereof; and (d) from about 5 to about 75% volume/volume percent of co-solvent.

8. The method of claim 7 wherein (b) is from about 10 to about 30 mg of dextromethorphan hydrobromide and (c) is from about 5 to about 12 mg of dyclonine or a pharmaceutically-acceptable salt thereof and wherein said composition has a pH of less than about 5.

9. The method of claim 8 wherein said co-solvent in (d) is a member selected from the group consisting of ethyl alcohol, glycerin, propylene glycol, polyethylene glycol and mixtures thereof.

10. A method of treating colds and associated sore throat in a human afflicted with same which comprises orally administering to said human, by direct swallowing, of at least one 5-30 ml dose of a liquid pharmaceutical composition of matter comprising, per 5-30 ml dose:

(a) from about 20 to about 75% of water by weight/volume;

(b) an effective antitussive amount of an oral antitussive drug selected from the group consisting of dextromethorphan, acid addition salts of dextromethorphan, chlophendianol hydrochloride, carbetapentane citrate, caramiphen edisylate, diphenydramine, diphenhydramine hydrochloride, noscapine hydrochloride, codeine, codeine sulfate, codeine phosphate, hydrocodone, hydrocodone bitartrate, and hydromorphone hydrochloride;

(c) from about 5 to about 100 mg of dyclonine or a pharmaceutically-acceptable salt thereof; and (d) from about 5 to about 75 volume percent of a co-solvent.

11. The method of claim 10 wherein (b) is from about 10 to about 30 mg of dextromethorphan hydrobromide and (c) is from about 5 to about 12 mg of dyclonine or a pharmaceutically-acceptable salt thereof and wherein said composition has a pH of less than about 5.

12. The method of claim 11 wherein (a) is from about 20 to about 40% by weight of water.

* * * * *